(12) United States Patent
Deutschendorf et al.

(10) Patent No.: US 10,758,110 B2
(45) Date of Patent: Sep. 1, 2020

(54) ENDOSCOPE AND METHOD FOR PRODUCING AN ENDOSCOPE, AND LATCHING ELEMENT

(71) Applicant: Karl Storz SE & Co. KG, Tuttlingen (DE)

(72) Inventors: Andreas Deutschendorf, Spaichingen (DE); Johannes Eisenlauer, Weilheim (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 71 days.

(21) Appl. No.: 15/602,921

(22) Filed: May 23, 2017

(65) Prior Publication Data

US 2017/0347861 A1    Dec. 7, 2017

(30) Foreign Application Priority Data

Jun. 1, 2016    (DE) .......................... 10 2016 110 114

(51) Int. Cl.
| | |
|---|---|
| *G02B 9/00* | (2006.01) |
| *A61B 1/00* | (2006.01) |
| *A61B 1/002* | (2006.01) |
| *G02B 23/24* | (2006.01) |

(52) U.S. Cl.
CPC .......... *A61B 1/00105* (2013.01); *A61B 1/002* (2013.01); *A61B 1/0011* (2013.01); *G02B 23/2423* (2013.01); *G02B 23/2446* (2013.01); *G02B 23/2453* (2013.01); *G02B 23/2476* (2013.01); *G02B 23/2469* (2013.01)

(58) Field of Classification Search
CPC ................................................. A61B 1/00105
USPC .......................................................... 359/738
See application file for complete search history.

(56) References Cited

U.S. PATENT DOCUMENTS

| | | | |
|---|---|---|---|
| 4,148,551 A | | 4/1979 | MacAnally |
| 4,771,766 A | * | 9/1988 | Aoshiro ................. A61B 1/121 600/155 |
| 8,852,087 B2 | * | 10/2014 | Meyer ................ G02B 23/2423 600/171 |
| 2014/0066714 A1 | | 3/2014 | Terliuc |
| 2018/0333044 A1 | * | 11/2018 | Jenkins .............. A61B 1/00105 |

FOREIGN PATENT DOCUMENTS

| | | |
|---|---|---|
| DE | 1977884 U | 2/1968 |
| DE | 19804234 C1 | 11/1999 |
| EP | 2453288 A1 | 5/2012 |

OTHER PUBLICATIONS

German Search Report Application No. 10 2016 110 114.1 Completed Date: Mar. 3, 2017; dated Mar. 8, 2017 8 Pages.
German International Search Report Application No. 17171299.5 Completed: Oct. 31, 2017; dated Nov. 13, 2017 9 Pages.

\* cited by examiner

*Primary Examiner* — James C. Jones
(74) *Attorney, Agent, or Firm* — Whitmyer IP Group LLC

(57) ABSTRACT

An endoscope having an elongate shaft and a system tube, which extends inside the shaft and in which an image carrier is arranged, the system tube is held in an axial direction of the shaft by means of at least one resilient latching element, and a method for producing such an endoscope and to a latching element for such an endoscope.

17 Claims, 6 Drawing Sheets

ENDOSCOPE AND METHOD FOR PRODUCING AN ENDOSCOPE, AND LATCHING ELEMENT

TECHNICAL FIELD

The present invention relates to an endoscope, a method for producing an endoscope, and a latching element for a corresponding endoscope.

BACKGROUND

Endoscopes are used nowadays for many applications in medicine and technology. An endoscope typically comprises an elongate shaft and an endoscope head arranged at the proximal end of the shaft (i.e. the end near the observer). The shaft can in particular be rigid and can have a rigid outer tube. In order to generate an image of an object field in the cavity, an endoscope objective is arranged in the distal end area of the shaft (the end away from the observer). By way of an image carrier arranged in the interior of the shaft, the endoscopic image can be conveyed to the endoscope head, where it is made available, for example, for viewing by the observer. Moreover, an illumination light guide can be arranged inside the shaft in order to transport illumination light to the distal end of the endoscope. Such an endoscope is also referred to as "endoscope optics".

The image carrier, which can be formed for example by a number of successive rod lenses, is generally received in an elongate tube, which is also referred to as "system tube" or "optics tube" and which, in the production of the endoscope, is pushed into the outer tube or into an inner tube of the shaft arranged inside the outer tube. After it has been pushed in, the system tube is fixed in the axial direction inside the endoscope, for example with grub screws or by welding. This takes quite a lot of time, and it is not always possible to remove the system tube again, for example for repair purposes.

It is known from EP 2 453 288 A1 that an objective mount is loaded in the distal direction by a compression spring, wherein an abutment for the compression spring is designed as a slotted, spring-elastic sleeve. The distal edge of the sleeve has a peripheral locking projection which, in the assembled state, engages in a peripheral latching groove in the endoscope housing. The compression spring presses the objective mount in the distal direction against a shoulder in the endoscope housing, in order to place the objective in a stable axial position in the endoscope housing. The sleeve is designed tapering conically in the proximal direction. To release the latching connection, a dismantling tube can be pushed onto the conical outer wall of the sleeve, between the sleeve and the endoscope housing. A system tube with an image carrier is not fixed by this. The conically shaped, spring-elastic sleeve and the interspace required for insertion of the dismantling tube occupy a part of the available lumen in the distal end area of the shaft, thereby limiting the space available for the image carrier, which is a disadvantage particularly in the case of thin endoscopes.

It is an object of the present invention to make available an endoscope and a method for producing an endoscope, and also a latching element for a corresponding endoscope, wherein the abovementioned disadvantages are avoided as far as possible, and wherein in particular a simplified assembly is permitted with simple axial fixing of the system tube.

SUMMARY

This object is achieved by an endoscope, by a method, and by a latching element according to the present invention.

Advantageous developments of the invention are set forth in the dependent claims.

An endoscope according to the invention, which can also be designated as endoscope optics, has an elongate shaft which is suitable in particular for insertion into an internal cavity of a human or animal body or also into a cavity of a technical object and which is preferably rigid. An objective for generating an image of an object field, for example a cavity inside the body, is generally arranged in a distal end area of the shaft. Moreover, the endoscope can have an endoscope head arranged at the proximal end of the shaft. The endoscope can be sealed off hermetically and is sterilizable, preferably autoclavable.

The endoscope moreover has a system tube which extends at least with part of its length inside the shaft, in particular inside an outer tube of the shaft. The system tube can be guided directly in the outer tube or, for example, by means of one or more further components of the endoscope that are arranged in the outer tube. Arranged inside the system tube is an image carrier, which is formed in particular by a rod lens arrangement, for example by one or more relay lens systems, or by a coherent bundle of optical fibers. The image carrier serves to carry an endoscopic image, captured in the distal end area of the shaft, for example the image of the object field of the inner cavity of the body created by the objective, in the proximal direction, where the image can be viewed or otherwise evaluated. The image carrier can in particular extend in the proximal direction beyond the proximal end of the system tube.

According to the invention, the system tube is held relative to the shaft, in an axial direction of the shaft, by means of at least one resilient latching element. For this purpose, the resilient latching element can have one or more spring-elastic latching portions or can itself be spring-elastic overall. The latching element creates a latching connection between the system tube and the shaft, if appropriate via further components. Preferably, the system tube is held by the resilient latching element at least against displacement in a proximal direction. In the radial direction, the system tube can be otherwise held or secured, for example by a narrow-tolerance fit. It is likewise possible to provide fixing in respect of rotation of the system tube about its longitudinal axis.

By virtue of the fact that the system tube is held in an axial direction of the shaft in the endoscope by means of at least one resilient latching element, it is easily possible to secure the system tube axially at a predetermined position, which can be defined, for example, by the function of the optical system of the endoscope. The latching connection by means of a resilient latching element permits particularly straightforward assembly in which the system tube can be fixed in the axial direction by the resilient engagement of the latching element, which generates the latching connection between the system tube and the shaft. In particular, it is possible for the system tube to be inserted into the endoscope housing in a single work step or in a reduced number of work steps and to secure it there in the axial direction by the engagement of the latching element. Complicated fixing by screwing or welding can thus generally be omitted.

According to a preferred embodiment of the invention, the resilient latching element forms an abutment for a spring element, which loads the system tube in a distal axial direction against a limit stop. The spring element can engage directly on the system tube or can load the latter in the distal direction via one or more components connected to the system tube, for example via a coupling element connected fixedly to the system tube. The system tube is pressed by the spring element against the limit stop which limits the movement of the system tube in the distal direction. The spring element can be designed, for example, as a compression spring, which is supported at the proximal side on the latching element and at the distal side on the system tube or on the coupling element connected to the system tube. By virtue of the fact that the system tube is pretensioned against the limit stop with a spring force by the spring element bearing on the latching element, it is easily possible to limit the depth of insertion when pushing the system tube into the shaft and at the same time to fix the system tube in a manner free of play in an axial direction, wherein the force acting in the axial direction can be predetermined by the design and compression of the spring element.

The limit stop against which the system tube is loaded in the distal direction is preferably formed in the distal end area of the shaft. The system tube is pretensioned relative to the shaft in the distal direction and is thus fixed relative to the distal end area of the shaft. It is thus possible to ensure that the system tube, and with it the image carrier arranged therein, adopts a predetermined axial position in the distal end area, which position, for example, can be defined with respect to structural elements of the objective. It is thereby possible to achieve particularly effective fixing of the image carrier and therefore an improved quality of the image that is carried.

In a particularly preferred manner, the limit stop against which the system tube is pretensioned in the distal direction is formed by a cover glass which is secured in the distal end area of the shaft. The system tube bears on the cover glass in particular via an objective, wherein the objective is arranged between the cover glass and the image carrier. The objective can be connected partially to the cover glass and/or partially to the system tube. In particular, an objective sleeve in which one or more optical components of the objective are received, can be connected fixedly to the system tube and continue the latter in the distal direction; one or more further optical components can bear on the cover glass or are supported directly or indirectly thereon. The cover glass, which can be designed for example as a plane-parallel plate, serves in particular for tight distal sealing of the shaft and can be inserted tightly into the distal end of an outer tube or of an inner tube of the shaft. In this way, the assembling of the endoscope and the axial securing of the system tube are further simplified.

According to a particularly preferred embodiment of the invention, the endoscope has an endoscope head, which is arranged at a proximal end of the shaft. The endoscope head is generally not provided for insertion into the cavity and can protrude radially beyond the outer contour of the shaft or beyond the outer tube of the shaft. An image-viewing facility can be provided in the endoscope head, for example an eyepiece for viewing the image that has been carried. The endoscope head has a housing which is preferably fixedly connected to the proximal end of the shaft, for example to an outer tube of the shaft. According to this embodiment, the system tube extends into the endoscope head, and the resilient latching element is arranged inside the endoscope head and connects a proximal end area of the system tube to the housing of the endoscope head. The latching connection created by the latching element is present in particular between the proximal end area of the system tube, or a coupling element fixedly connected thereto, and the housing, or a component fixedly connected to the latter. In this way, use can advantageously be made of the fact that the endoscope head can protrude radially in relation to the shaft, and that more space is therefore available for the resilient latching element in the endoscope head than inside the outer tube of the shaft. Since the external diameter of the shaft is generally predefined by the intended use of the endoscope, it is thus possible to fix the system tube inside the endoscope by means of the latching element, without having to reduce the external diameter of the system tube or the cross section available for the image carrier.

The latching element is preferably latched in at least one latching recess on an inner face of an inner sleeve of the endoscope shaft connected fixedly to the housing of the endoscope head. For this purpose, for example, latching portions of the latching element, or the latching element as a whole, can be engaged in the at least one latching recess by a spring force and can thereby create the latching connection between the system tube and the endoscope head. The latching recess can be formed, for example, as an indent introduced into the inner face of the inner sleeve, in particular as an at least partially circumferential groove or non-continuous groove. The latching element can be inserted in an interspace between the inner sleeve and the coupling element. This allows the system tube to be fixed in the endoscope in a simple, secure and space-saving way.

The system tube is preferably held releasably by means of the resilient latching element. In particular, the system tube is held releasably in the endoscope by means of the latching element and can be removed after the latching connection has been released, for example withdrawn in the proximal direction from an outer tube of the shaft and from the endoscope head. For this purpose, provision can in particular be made that the latching element can be unlatched from its latching position by elastic deformation and removed in the proximal direction. A correspondingly shaped tool may be needed for this. In this way, it is easier to replace or repair the system tube or the optical elements received in the latter.

The latching element is preferably formed in one piece. The resilient latching element is designed in particular as a plastic clip and made from a plastic material, for example from polyether ether ketone (PEEK). However, the resilient latching element can also be made, for example, of a suitable metallic material, for example titanium. The production can be simplified in this way, and it is thereby additionally achieved that the latching element permanently retains its spring-elastic property and withstands the temperature loads acting on endoscopes, for example during autoclaving.

According to a preferred embodiment of the invention, the resilient latching element is designed as a latching sleeve having one or more latching hooks which are arranged radially on the outside and which are radially inwardly resilient. The latching hooks can latch spring-elastically into the at least one latching recess of the inner sleeve of the endoscope head. The latching sleeve is preferably substantially cylindrical both on the inside and on the outside and is thickened annularly at the proximal edge and is designed, at the distal edge, with the outwardly protruding latching hooks. The sleeve-shaped latching element according to this embodiment can be annularly closed at the proximal end for example, but can have slits at the distal end which divide the distal portion of the latching sleeve into a plurality of resilient latching segments, which each have, at their distal edge, the outwardly protruding latching hooks. The distal side of the latching sleeve can serve as an abutment for the compression spring, which loads the system tube in the distal direction. A latching element of this kind can be produced easily and permits secure and simple fixing of the system tube in the axial direction. Moreover, such a latching sleeve can permit release of the fixing in order to remove the system tube from the endoscope housing, for example by the latching segments of the latching sleeve being pressed together until the latching hooks are disengaged from the latching recesses, or from the latching groove, and the latching sleeve can be withdrawn.

According to a further preferred embodiment of the invention, the resilient latching element is designed as a resilient clamping ring. The resilient clamping ring can be designed, for example, as a non-continuous ring or also in the manner of a retainer ring and can be elastically compressible in its interrupted area in order to reduce the external diameter of the clamping ring; this facilitates the insertion of the clamping ring into the endoscope housing. In order to fix the system tube, the clamping ring engages with elastic recovery in the at least one latching recess, for example in the latching groove on the inner face of the inner sleeve of the endoscope head. In this way, a particularly simple embodiment is obtained which likewise permits secure and simple fixing of the system tube in the axial direction. Moreover, this can permit release of the fixing in order to remove the system tube from the endoscope housing, for example by means of the clamping ring being pressed together until it unlatches from the latching groove and can be withdrawn in the proximal direction. For this purpose, in the case of a clamping ring designed as a non-continuous ring, eyelets can be arranged at the two ends of the ring, which eyelets can be gripped with a suitable tool and drawn together.

Provision can advantageously be made that the resilient latching element has one or more latching lugs for securing the system tube against an axial rotation with respect to the endoscope housing. These latching lugs can be arranged on the inside and/or outside and do not go all the way round. The system tube, or the coupling element connected thereto, can have corresponding recesses into which the latching grooves on the inside engage; the endoscope housing, or the inner sleeve connected thereto, can likewise have recesses into which latching lugs arranged on the outside engage, which latching lugs at the same time can serve as latching hooks for the axial fixing. This can allow improved adjustment for achieving an improved image quality of the endoscope.

The resilient latching element preferably has at least one peripheral sealing element, for example an O-ring or a sealing lip. The sealing element can bear, for example, on an annular portion of a latching element designed as latching sleeve, such that, when the latching element is located in a latching position in order to produce the latching connection, the sealing element tightly seals off the interspace into which the latching element is fitted. It is thus possible for the latching element at the same time to seal off an interior of the endoscope against entry of moisture. Such sealing may be advantageous, in addition to a closed design of the endoscope head, for avoiding entry of moisture into the optical system.

The latching element can advantageously have one or more recesses for receiving drying elements composed of a suitable desiccant. If, upon insertion of the latching element, the latter is filled with the desiccant or the drying elements, it is thus easily possible to obtain improved protection against misting of optical components by any moisture that has entered. This applies especially if the latching element additionally has a peripheral sealing element.

In a method according to the invention for producing an endoscope which comprises an elongate shaft and an endoscope head arranged at a proximal end of the shaft, an endoscope housing is made available which comprises an outer tube of the shaft and the endoscope head connected thereto at the proximal end of the shaft. The endoscope head comprises an inner sleeve, which has at least one latching recess on its inner face, which latching recess can be designed for example as an at least partially circumferential groove. The endoscope head can have a housing inside which the inner sleeve is arranged. The outer tube, the housing of the endoscope head and the inner sleeve are preferably pre-assembled as a group and fixedly connected to one another when making available the endoscope housing. The endoscope housing made available can comprise further components which are likewise already pre-assembled, for example an attachment piece for attaching a fiber optic cable with which illumination light can be delivered from a separate light source, and illumination light guides for carrying the illumination light to the distal end of the shaft.

A system precursor is likewise made available as a pre-assembled group, said system precursor comprising a system tube with an image carrier received therein, and a coupling element fixedly connected to the proximal end of the system tube. The image carrier can be designed as a rod lens arrangement for example, wherein the rod lenses, with spacers arranged between them, are arranged one after another in the system tube. One or more lens elements of an objective are preferably received in the distal end area of the system tube, or in an objective sleeve connected to the system tube at the distal end of the latter, said lens elements being adjoined in the proximal direction by the image carrier or the rod lens arrangement. The coupling element is preferably substantially sleeve-shaped and is placed onto the outside of the proximal end area of the system tube. The system precursor can comprise further pre-assembled components connected to the system tube.

According to the invention, a compression spring, for example a helical spring, is pushed onto the coupling element from a proximal direction, wherein the travel of the compression spring is limited by an abutment of the coupling element, which abutment can be formed, for example, as an external annular collar. Moreover, a resilient latching element is pushed onto the coupling element from a proximal direction, such that the compression spring is arranged between the abutment of the coupling element and the latching element. Moreover, an eyepiece mount is screwed onto the proximal end of the coupling element. The eyepiece mount can have a substantially sleeve-shaped design, for example, and, in its distal end area, it can carry an outer thread with which the eyepiece mount is screwed into a corresponding inner thread of the coupling element. The eyepiece mount can be designed in such a way that, by screwing on the eyepiece mount, the latching element and also the compression spring held by the latter are secured against being lost. The group assembled in this way, comprising the system precursor, the compression spring, the latching element and the eyepiece mount, is designated below as the optics unit.

In a further assembly step, the optics unit, and thus the system precursor, is pushed into the endoscope housing in a distal direction as far as a limit stop. After being pushed in, the system tube is arranged inside the outer tube but reaches with its proximal end area into the endoscope head. The coupling element, which is connected to the proximal end of the system tube, and the compression spring pushed onto it, and the latching element, are now arranged inside the housing of the endoscope, at least partially also inside the inner sleeve of the endoscope head. The limit stop limiting the depth of insertion of the system tube in the distal direction is preferably situated in the distal end area of the shaft.

Moreover, the resilient latching element is displaced in the distal direction until it latches into the at least one latching recess of the inner sleeve. For this purpose, the inner sleeve can be shaped conically in a proximal portion, such that the resilient latching element is pressed together as it advances; by pushing it into the conically tapering portion of the inner sleeve, the latching segments, for example, of a latching element designed as a latching sleeve are thus pressed radially inward, or the ends of a clamping ring designed as a non-continuous ring are pressed together. When the at least one latching recess is reached, the elastic recovery of the latching element causes it to latch into the latching recess such that, for example, the latching lugs of the latching sleeve, or the clamping ring itself, then engage in the latching recess and hold the optics unit in the axial direction. The optics unit is thus held by the latched latching element against displacement in the proximal direction, while the aforementioned limit stop limits a displacement in the distal direction.

Through the interaction of the latched latching element with the compression spring and with the limit stop, the system precursor and the optics unit as a whole are thus easily secured in their axial position. The force acting on the limit stop via the system tube can be limited by the design of the compression spring. The method according to the invention permits a simplified assembly of the optics unit in the endoscope housing, for example without screwing or welding for fixing the system precursor. In this way, it is possible in particular for the endoscope housing and the system precursor or the optics unit to be produced separately and pre-assembled and thereafter joined to each other with minimal adjusting and assembling work.

According to a preferred embodiment of the invention, the endoscope housing comprises an inner tube, which extends in the outer tube of the shaft and which is fixedly connected to the inner sleeve of the endoscope head; illumination light guides, for example, can be received in an interspace between the outer tube and the inner tube. Thus, when the pre-assembled optics unit is pushed into the pre-assembled endoscope housing, the system tube is pushed into the inner tube until the system tube reaches the limit stop for the system tube. The limit stop can advantageously be formed by a cover glass secured in the distal end area of the inner tube. The system tube or the optics unit is in this case pushed into the inner tube until the distal end of the system tube, or a component connected thereto, for example an objective sleeve or a lens element of the objective held by the objective sleeve, bears on the cover glass or on a component supported on the cover glass. By the resilient latching element being pushed in until it latches in the at least one latching recess, the system tube is thus pretensioned against the cover glass by the compression spring. It is in this way possible to achieve particularly simple and secure fixing of the system tube in the axial direction.

It is moreover preferable that an eyepiece is inserted into the eyepiece mount; this can be done before or after the eyepiece mount is screwed onto the proximal end of the coupling element. The eyepiece can be composed of an eyepiece sleeve and of one or more eyepiece lenses received in the latter. After the eyepiece mount has been screwed on and before the optics unit is pushed into the endoscope housing, the eyepiece is adjusted relative to the rest of the optical system, in particular relative to the image carrier; for this purpose, the eyepiece mount can comprise suitable adjusting means, for example adjusting screws. The optics unit, which is pushed into the endoscope housing in the next step, in this case also comprises the eyepiece, which is already adjusted. This permits further simplification of the assembling of the endoscope.

In addition to the production steps mentioned, further production steps can be provided. In particular, after the optics unit has been fixed in the endoscope housing by engagement of the latching element, the endoscope head can be closed by an eyepiece cup and an eyepiece cover glass being fitted proximally and being tightly connected to the housing of the endoscope head. The endoscope is preferably sealed off hermetically.

Moreover, according to the present invention, particularly simple disassembly of the endoscope may be permitted. For this purpose, provision can be made that the housing of the endoscope head can be opened proximally, such that the eyepiece mount is made accessible. For disassembly of the endoscope, the eyepiece mount can then be unscrewed from the coupling element. By compressing the latching element, for example the latching segments of a latching sleeve or the ends of a clamping ring designed as a non-continuous ring, the latching element can be unlatched from the at least one latching recess of the inner sleeve and pulled out in the proximal direction from the interspace between the inner sleeve and the coupling element; a suitably designed tool may be needed for this purpose. After the latching element has been removed, the system precursor can then be withdrawn from the endoscope housing. In this way, the system precursor can be replaced or repaired particularly easily.

A latching element according to the invention for an endoscope is designed as a resilient latching element for producing a latching connection in order to hold the system tube of an endoscope in an axial direction of the shaft of the endoscope. In particular, the latching element is designed as described above.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of two preferred illustrative embodiments and from the attached drawing, in which.

DETAILED DESCRIPTION

Figure 1:
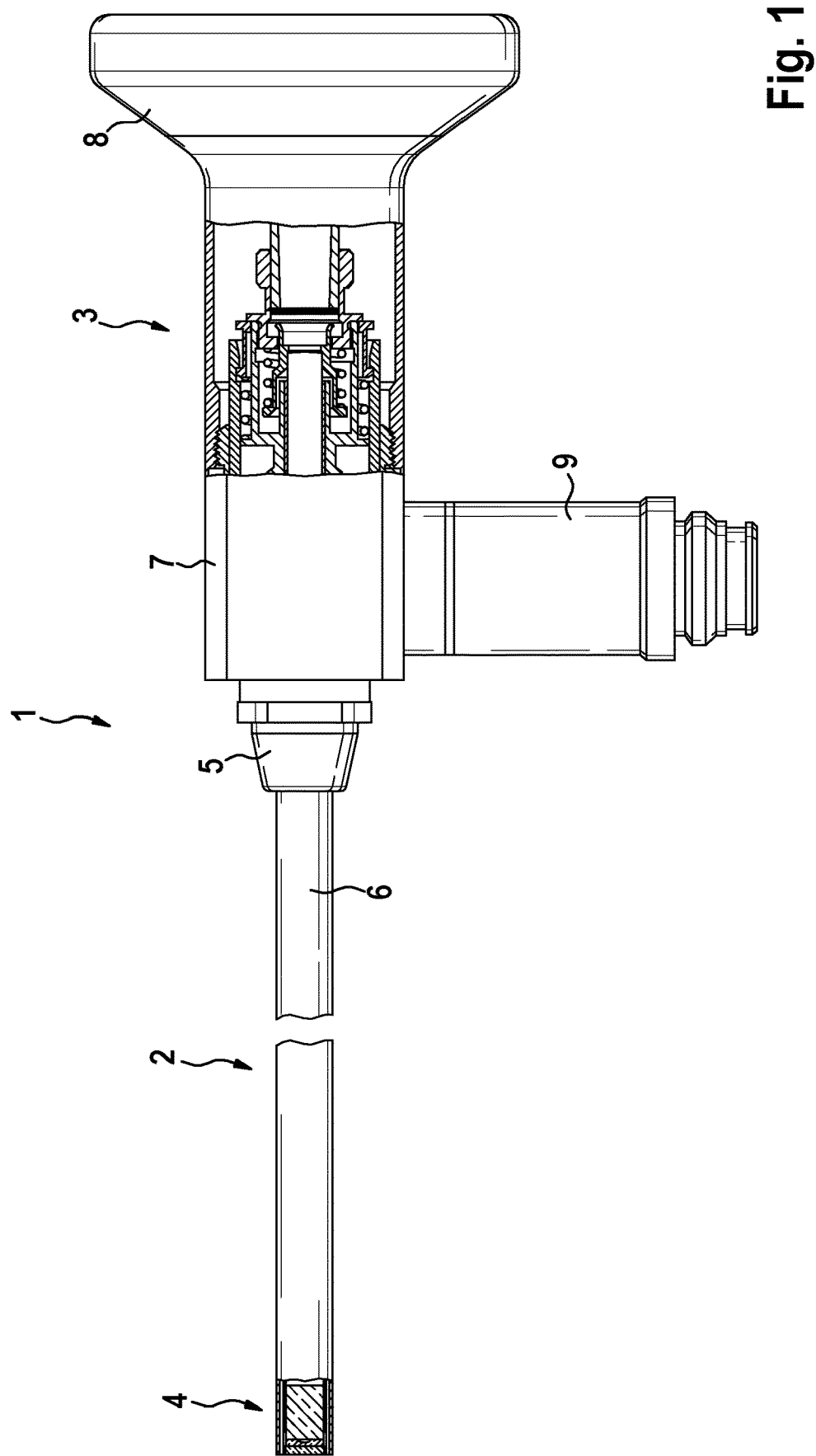
FIG. 1 shows a first illustrative embodiment of an endoscope according to the invention in a partially sectioned side view.

FIG. 1 shows an endoscope according to a first embodiment of the invention in a partially sectioned side view. The endoscope 1 comprises an elongate shaft 2 and an endoscope head 3 arranged at the proximal end of the shaft 2. The distal end area 4 of the endoscope shaft 2 is shown in section in FIG. 1. The endoscope head 3, which is likewise shown partially sectioned in FIG. 1, is connected to an outer tube 6 of the shaft via a cone 5. The endoscope head 3 has a housing 7, at the proximal end of which an eyepiece cup 8 is fitted. The housing 7 of the endoscope head 3 also carries a light attachment piece 9. In the parts of the endoscope shown in section in FIG. 1, further components are indicated which are shown enlarged in FIGS. 2 to 5 and which are described in more detail below.

Figure 2:
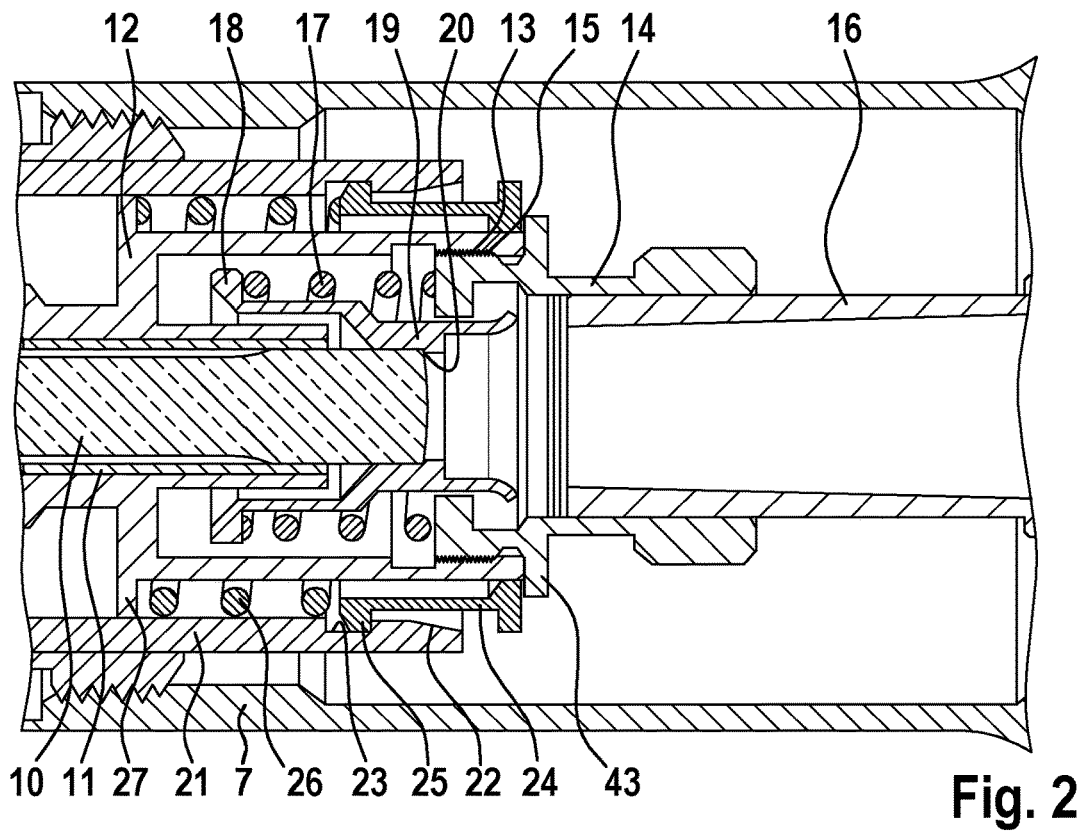
FIG. 2 shows a part of the internal structure of the endoscope head of the endoscope according to FIG. 1 in a longitudinal section.

FIG. 2 shows a part of the internal structure of the endoscope head 3 of the endoscope 1 in longitudinal section. In the illustrative embodiments of the invention described here, the image carrier is configured as a system of rod lenses arranged one after another, of which the proximal portion of the proximal rod lens 10 can be seen in FIG. 2. The rod lens 10, tapered in its central portion, is received in a system tube 11 which also receives the rod lenses which are arranged further in the distal direction and which are not shown in FIG. 2. The system tube 11 is connected by welding to an approximately sleeve-shaped coupling element 12 attached to the proximal end of the system tube 11. In its proximal end area, the outer sleeve-shaped part of the coupling element 12 has an inner thread 13 into which an approximately sleeve-shaped eyepiece mount 14 with an outer thread 15 is screwed. An eyepiece sleeve 16, which comprises optical elements (not shown in FIG. 2) of the eyepiece, is held adjustably in the eyepiece mount 14. An optics spring 17 configured as a helical compression spring bears on the distal side of the eyepiece mount 14 and is supported distally on an annular collar 18 of a rod lens mount 19. The proximal end of the proximal rod lens 10 of the image carrier is held in the rod lens mount 19. By way of a spacer (not shown in FIG. 2), which bears on a shoulder 20 of the rod lens mount, the rod lens 10 is loaded in the distal direction by the optics spring 17; the distal side of the eyepiece mount 14 here serves as an abutment for the optics spring 17. Since the further rod lenses following the rod lens 10 in the distal direction bear on the rod lens 10 and on each other via spacers, the entire rod lens system is thus pretensioned in the distal direction against a distal limit stop of the rod lens system and is thereby fixed in the axial direction. In the radial direction, i.e. in the transverse direction of the endoscope 1, the rod lens 10 and the further rod lenses and components can be fixed by narrow tolerances.

As is also shown in FIG. 2, an inner sleeve 21, which is fixedly connected to the housing 7, is arranged in the housing 7 of the endoscope head 3. In its proximal end portion, the inner sleeve 21 has, on the inside, a distally narrowing conical taper 22, in the distal direction from which a circumferential latching groove 23 is arranged, which is configured as an indentation in the inner face of the inner sleeve 21. A latching element, which is configured as a latching sleeve 24 in the illustrative embodiment shown, is pushed onto the outside of the coupling element 12. The latching sleeve 24 is closed annularly in its proximal end area and has, in its distal end area, resiliently held latching hooks 25, which engage in the latching grove 23. As is also shown in FIG. 2, the distal side of the latching sleeve 24 forms an abutment for a compression spring 26 which is configured as a helical spring and which is supported distally on an annular collar 27 of the coupling element 12. Since the latching sleeve 24 is held in the groove 23 against displacement in the proximal direction, the coupling element 12, and thus the system tube 11, is pressed in the distal direction by the compression spring 26 against a limit stop (described further below) for the system tube 11 and is thereby fixed in the axial direction. The forces required for fixing the components and acting on the rod lens system or the system tube 11 can be adjusted through the design of the optics spring 17 and of the compression spring 26.

Figure 3:
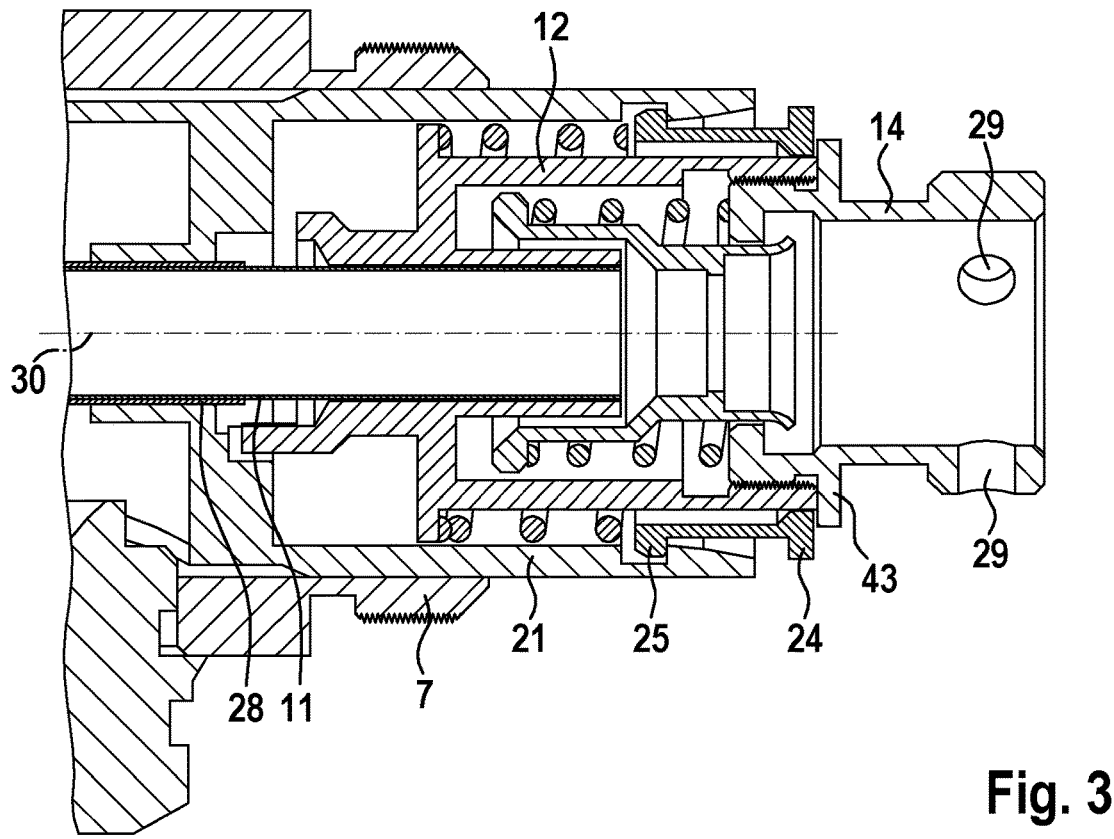
FIG. 3 shows a part of the internal structure of the endoscope head of the endoscope according to FIG. 1 in a sectioned side view.

FIG. 3 shows the internal structure of the endoscope head 3 in a sectioned side view, in which the housing 7 of the endoscope head 3, composed of several components, is depicted only partially. As is shown in FIG. 3, the inner sleeve 21 is fixedly connected to the housing 7. The inner sleeve 21 is in turn fixedly connected, for example soldered, to an inner tube 28 in which the system tube 11 is guided. In FIG. 3, moreover, two of three adjusting bores 29 can be seen into which adjusting screws can be inserted in order to adjust the eyepiece sleeve 16 relative to the rod lens 10 or relative to the optical axis 30. The rod lens 10 and the eyepiece sleeve 16 are not shown in FIG. 3.

Figure 4:
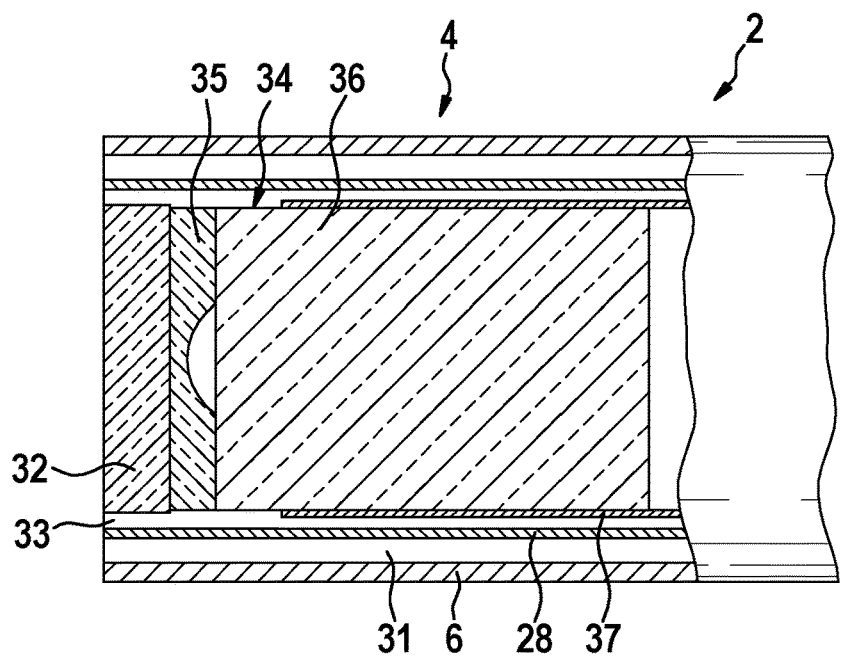
FIG. 4 shows the distal end of the shaft of the endoscope according to FIG. 1 in a partially sectioned side view.

FIG. 4 shows the distal end area 4 of the shaft 2 of the endoscope 1 according to FIG. 1 in an enlarged view and in section. As can be seen from FIG. 4, the inner tube 28 extends inside the outer tube 6. Illumination light guides (not shown) are arranged in the interspace 31 between the outer tube 6 and the inner tube 28. Serving as a distal closure of the lumen surrounded by the inner tube 28, a cover glass 32 is soldered into the inner tube 28. For the sake of clarity, the interspace 33, filled with solder, is shown wider in FIG. 4. The cover glass 32 is followed in the proximal direction by the objective 34 and the rod lenses of the image carrier (not shown in FIG. 4). The objective 34 comprises a first objective lens 35 and an objective lens unit 36, which comprises further lens elements not shown in detail in FIG. 4. The cover glass 32, the objective lens 35 and said further lens elements can be separated from one another by spacers (not shown in FIG. 4). The objective lens unit 36 is inserted fixedly by adhesive bonding into an objective sleeve 37, which is fixedly connected to the distal end of the system tube 11, the latter not necessarily extending into the end area 4 shown in FIG. 4.

As has been described in connection with FIG. 2, the rod lens system is loaded by the optics spring 17 against a distal limit stop of the rod lens system. This limit stop, against which the rod lens system is axially fixed inside the system tube 11, is formed by the objective lens unit 36 fixedly connected to the distal end of the system tube 11. The system tube 11 is loaded by the compression spring 26 in the distal direction against a limit stop for the system tube 11, which limit stop is provided by the cover glass 32 fixedly held in the inner tube 28 or by the first objective lens 35 bearing on the cover glass 32, optionally via spacers. This limit stop for the system tube 11 is reached when the objective lens unit 36 bears, optionally via a spacer, on the first objective lens 35. In this way, the system tube 11 and the optical system received therein are fixed in the axial direction inside the endoscope 1.

Figure 5:
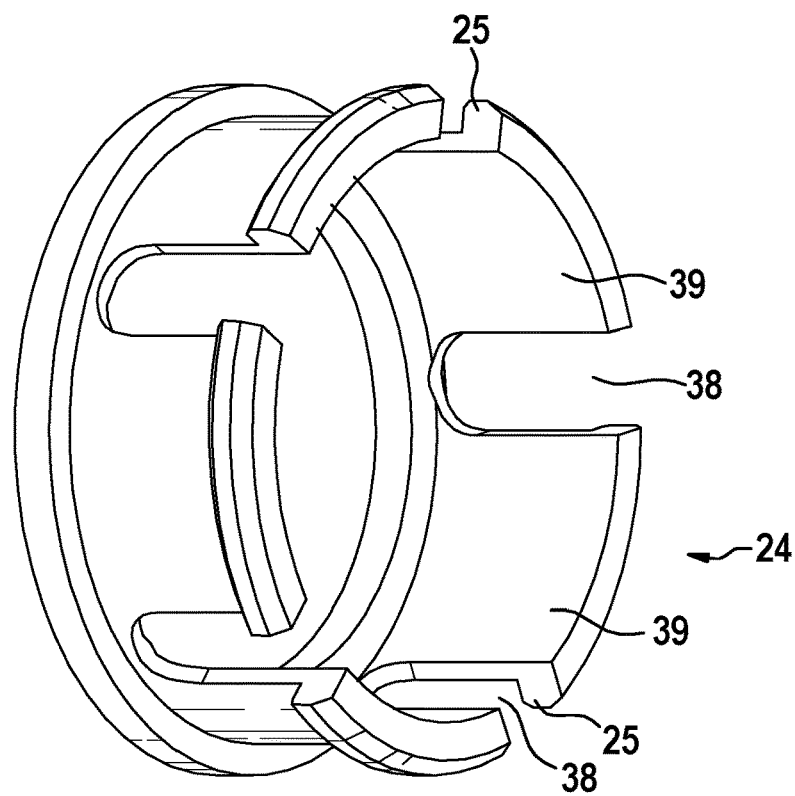
FIG. 5 shows the latching sleeve of the endoscope according to FIG. 1 in an oblique view.

FIG. 5 shows the latching sleeve 24 in an enlarged and oblique view, as seen from the distal direction. As can be seen from FIG. 5, the distal end of the latching sleeve 24 is divided by slits 38 into a plurality of resilient latching segments 39. At their distal end, the latching segments 39 carry the outwardly directed latching hooks 25. At the proximal end, the latching sleeve 24 is formed as a closed ring.

In the production of the endoscope 1 designed as described above, the endoscope housing, which comprises the outer tube 6, the housing 7 of the endoscope head 3, the inner sleeve 21 and the inner tube 28, is pre-assembled and made ready. The pre-assembled endoscope housing likewise comprises the light attachment piece 9 and the illumination light guides routed through the latter as far as the distal end area 4 of the endoscope 1, and, if appropriate, further components. Moreover, in the pre-assembled endoscope housing, the cover glass 32 is soldered into the inner tube 28 at the distal end thereof. Moreover, likewise as a pre-assembled group, the system precursor is made available, which comprises the system tube 11, the rod lenses and spacers received in the latter, the coupling element 12 welded to the system tube 11, and, if appropriate, further components. The system precursor also comprises the objective lens unit 36, which is adhesively bonded into the objective sleeve 37, wherein the objective sleeve 37 is fixedly connected to the distal end of the system tube 11. Moreover, an eyepiece assembly is made available which comprises the eyepiece mount 14, the rod lens mount 19 inserted into the latter and crimped at the proximal end, and the optics spring 17 arranged on the outside of the rod lens mount 19.

To assemble the endoscope 1, first the compression spring 26 and then the latching sleeve 24 are pushed onto the coupling element 12 from the proximal direction. The eyepiece mount 14 is then screwed with its outer thread 15 into the inner thread 13 of the coupling element, wherein the coupling element 12 is pulled against the disk 43 of the eyepiece mount 14. The proximal rod lens 10 is in this way placed under the pretensioning force exerted by the optics spring 17 via the rod lens mount 19, as a result of which the rod lens system is pressed against the objective lens unit 36 and thus fixed. After the eyepiece sleeve 14 has been screwed into the coupling element 12, the latching sleeve 24 bears on the disk 43 of the eyepiece mount 14 and is also secured by the latter against being lost. The eyepiece sleeve 16, with the eyepiece lenses received in it, is inserted into the eyepiece mount 14 and, by means of adjusting screws guided through the adjusting bores, is adjusted relative to the optical axis 30 of the rod lens system. The assembly made up of the system precursor with the compression spring 26 and the latching sleeve 24 and of the eyepiece group represents the optics unit of the endoscope 1, which comprises almost the entire optical system of the endoscope 1.

The optics unit is now pushed from the proximal direction into the pre-assembled endoscope housing, wherein the system tube 11 is pushed into the inner tube 28. The latching hooks 25 are pressed inward over the taper 22 of the inner sleeve 21 but do not yet latch in the latching groove 23. After the objective lens unit 26 connected to the inner tube 21 has reached the limit stop formed by the cover glass 32 and the first objective lens 35, the latching sleeve 24 is displaced farther in the proximal direction until the latching hooks 25 latch in the latching groove 23. The compression spring 26 is thus compressed, which thereby generates the force necessary for axially fixing the optics unit. The optics unit is in this way secured against axial displacement. Since the system tube 11 is guided inside the inner tube 28 with narrow tolerances, the optics unit as a whole is sufficiently fastened inside the endoscope 1; an adjustment or an additional locking is not needed. In addition, the optics unit can be fixed against a rotation about the longitudinal axis of the endoscope 1; however, this too can be omitted. Moreover, further work steps, such as the introduction of desiccant, can be carried out. Finally, the endoscope head 3 is tightly closed off by attachment of the eyepiece cup 8 and of the eyepiece cover glass.

To remove the system precursor, the endoscope head 3 can be opened and the eyepiece mount 14 can be unscrewed from the coupling element 12. The latching segments 39 of the latching sleeve 24 are pressed together via a tool pushed into the taper 22, until the latching hooks 25 disengage from the latching groove 23. The latching sleeve 24 can then be pulled off in the proximal direction, and the system precursor can be pulled out of the endoscope housing.

Figure 6:
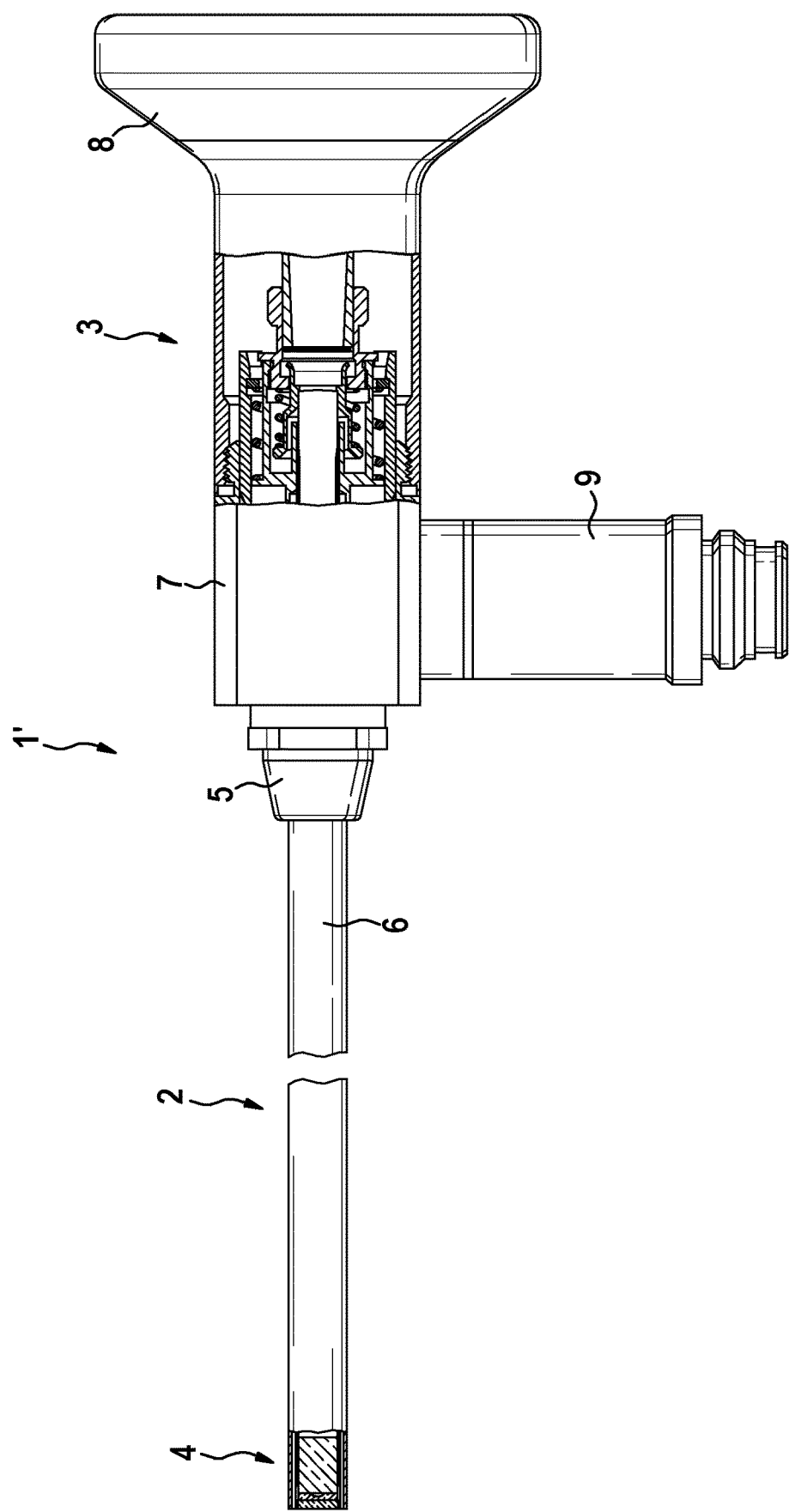
FIG. 6 shows a second illustrative embodiment of an endoscope according to the invention in a view corresponding to FIG. 1.
Figure 7:
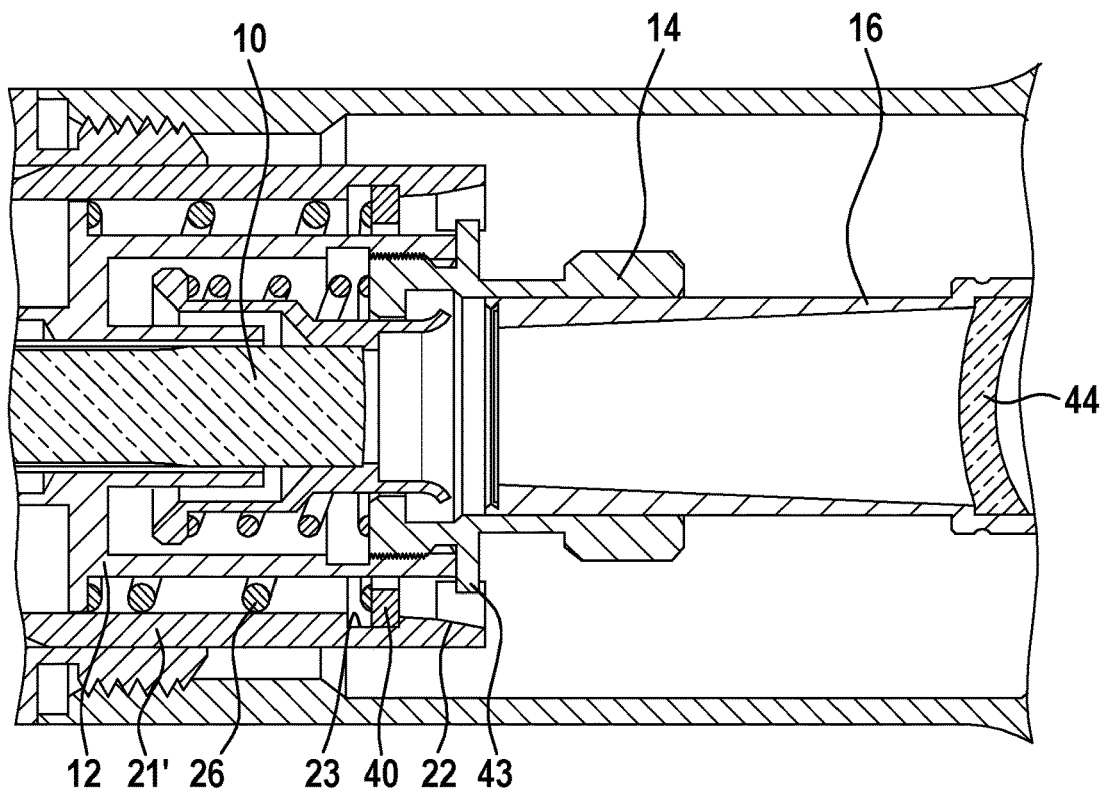
FIG. 7 shows a part of the internal structure of the endoscope head of the endoscope according to FIG. 6 in a longitudinal section.
Figure 8:
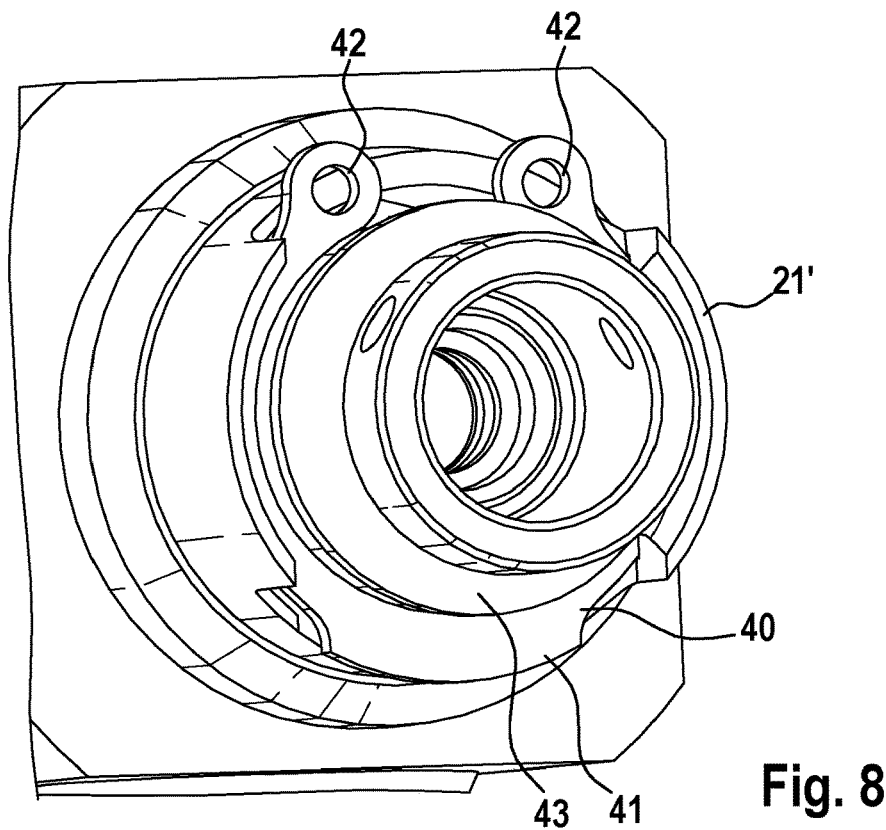
FIG. 8 shows a part of the internal structure of the endoscope head of the endoscope according to FIG. 6 in an oblique view.
Figure 9:
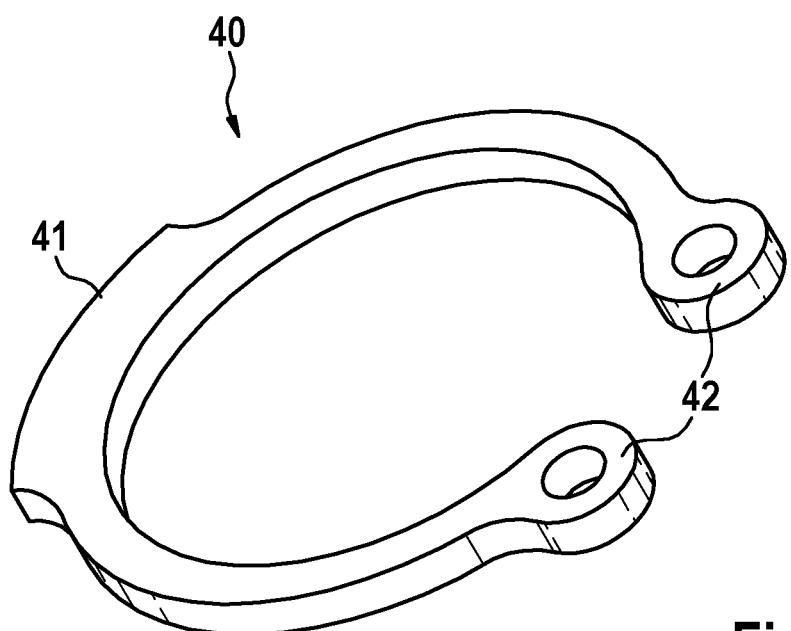
FIG. 9 shows the clamping ring of the endoscope according to FIG. 6 in an oblique view.

FIG. 6 shows, in a view corresponding to FIG. 1, an endoscope 1' according to a second illustrative embodiment of the invention. As is shown in the longitudinal section through the endoscope head 3 in FIG. 7, the latching sleeve 24 is here replaced by an elastically deformable clamping ring 40 configured as a non-continuous ring, which clamping ring 40 is latched in the latching groove 23 and, in a manner corresponding to that described above, serves as a proximal abutment of the compression spring 26 and fixes the optics unit in the endoscope housing. FIG. 7 moreover shows an example of an eyepiece lens 44 inserted into the eyepiece sleeve 16. As can be seen in FIG. 8, in an oblique view from the proximal direction, the latching groove 23 in this embodiment does not go all the way round, and instead the inner sleeve 21' has two circumferential interruptions through which there emerge a widened part 41 and two eyelets 42 of the clamping ring 40, which are arranged on both sides of the interruption of the clamping ring 40. The clamping ring 40 with the widened part 41 and the eyelets 42 is shown in an oblique view in FIG. 9. In other respects, the endoscope 1' according to the second illustrative embodiment of the invention is constructed like the above-described endoscope 1.

To produce the endoscope 1', the procedure followed is the one described in the first illustrative embodiment of the invention, with the endoscope housing, the system precursor and the eyepiece unit being made available correspondingly. The compression spring 26 and the clamping ring 40 are then pushed onto the coupling element 12. The eyepiece mount 14 is then screwed into the coupling element 12, after which the eyepiece sleeve 16 can be inserted and the eyepiece can be adjusted. The optics unit pre-assembled in this way can now be pushed into the endoscope housing until the objective lens unit 36, as described above, reaches the limit stop defined by the cover glass 32. The clamping ring 40, which is not yet latched in the latching groove 23 but instead bears on the disk 43 of the eyepiece mount 14, is then moved in the distal direction to permit latching. In doing this, the clamping ring 40 is pressed together over the taper 22 and finally latches in the latching groove 32 by means of elastic recovery. In a manner corresponding to that described for the first illustrative embodiment of the latching sleeve 24, the clamping ring 40 forms the distal abutment for the compression spring 26 which subjects the coupling element 12 and therefore the system tube 11 to the force necessary for axial fixing. In the transverse direction, the system tube 11 is held inside the inner tube 28 by narrow tolerances.

For disassembly, the eyepiece mount 14 can be unscrewed from the coupling element 12. The clamping ring 40 can then be contracted by pressing the eyelets 42 together by means of a tool, made to disengage from the latching groove

The invention claimed is:

1. An endoscope comprising:
    an elongate shaft; and
    a system tube that extends inside the shaft and in which an image transmitter is arranged;
    wherein the system tube is held in an axial direction of the shaft by at least one resilient latching element; and
    wherein the system tube is held releasably.

2. The endoscope according to claim 1, wherein the resilient latching element forms an abutment for a spring element, and the spring element loads the system tube in a distal direction of the elongate shaft against a limit stop.

3. The endoscope according to claim 2, wherein the limit stop is formed in a distal end area of the shaft.

4. The endoscope according to claim 3, wherein the limit stop is formed by a cover glass secured in the distal end area of the shaft; and
    the system tube bears against the cover glass via an objective arranged between the cover glass and the image transmitter.

5. The endoscope according to claim 1, further comprising:
    an endoscope head arranged at a proximal end of the shaft;
    wherein the system tube extends into the endoscope head, and the at least one resilient latching element is received in the endoscope head and connects a proximal end area of the system tube and a housing of the endoscope head.

6. The endoscope according to claim 5, wherein the at least one resilient latching element is latched in at least one latching recess formed on an inner face of an inner sleeve of the endoscope head.

7. The endoscope according to claim 1, wherein the at least one resilient latching element is designed as a latching sleeve with at least one resilient latching hook arranged on the outside.

8. The endoscope according to claim 1, wherein the at least one resilient latching element is designed as a resilient clamping ring.

9. The endoscope according to claim 1, wherein the at least one resilient latching element has at least one latching lug for securing against rotation.

10. The endoscope according to claim 1, wherein the at least one resilient latching element has at least one peripheral sealing element and at least one recess for receiving a desiccant.

11. A method for producing an endoscope, comprising the steps of:
    making available an endoscope housing including an outer tube of an elongate shaft and an endoscope head connected to a proximal end of the shaft, the endoscope head having an inner sleeve which includes at least one latching recess on an inner face thereof;
    making available a system precursor including a system tube with an image transmitter received therein, and a coupling element fixedly connected to a proximal end of the system tube;
    pushing a compression spring and a resilient latching element onto the coupling element from a proximal direction;
    screwing an eyepiece mount onto a proximal end of the coupling element;
    pushing the system precursor into the endoscope housing in a distal direction as far as a limit so that the system tube extends inside the shaft; and
    moving the latching element in the distal direction on the coupling element until the latching element latches into the at least one latching recess, thereby holding the system tube in an axial direction of the shaft;
    wherein the system tube is held releasably.

12. The method according to claim 11, wherein the endoscope housing further includes an inner tube which is arranged in the outer tube and which is fixedly connected to the inner sleeve of the endoscope head, wherein upon insertion of the system precursor into the endoscope housing, the system tube is pushed into the inner tube and the limit stop is formed in a distal end area of the inner tube.

13. The method according to claim 11, wherein an eyepiece is inserted into the eyepiece mount and is adjusted after the eyepiece mount has been screwed on and before the system precursor is pushed into the endoscope housing.

14. The method according to claim 12, wherein an eyepiece is inserted into the eyepiece mount and is adjusted after the eyepiece mount has been screwed on and before the system precursor is pushed into the endoscope housing.

15. An endoscope comprising:
    a shaft;
    a system tube that extends inside the shaft;
    an image transmitter arranged inside the system tube;
    a latching element that secures the system tube in an axial direction of the shaft;
    a limit stop formed by a cover glass secured in a distal end area of the shaft;
    a spring element that abuts the latching element and loads the system tube in a distal direction of the shaft against the limit stop;
    an endoscope head arranged at a proximal end of the shaft;
    the system tube extends into the endoscope head and the latching element connects the system tube to the endoscope head.

16. The endoscope of claim 15, wherein the image transmitter inside the system tube bears against the cover glass of the limit stop via an objective arranged between the system tube and the cover glass.

17. The endoscope of claim 16, wherein the endoscope head has a housing and an inner sleeve, and a recess is formed on an inner face of the inner sleeve; and
    the latching element releasably latches to the recess, thereby releasably connecting a proximal end area of the system tube with the housing of the endoscope head.

* * * * *